US010881083B2

(12) United States Patent
Sapir et al.

(10) Patent No.: US 10,881,083 B2
(45) Date of Patent: Jan. 5, 2021

(54) SYSTEM, METHOD AND COMPUTER PROGRAM PRODUCT FOR ANIMAL-BASED OLFACTORY DETECTION

(71) Applicant: ICTS EUROPE SAS, Tremblay-en-France (FR)

(72) Inventors: Oren Sapir, Kochav Yair (IL); Allen Goldblatt, Tel Aviv (IL)

(73) Assignee: ICTS EUROPE SA, Tremblay en France (FR)

(*) Notice: Subject to any disclaimer, the term of this patent is extended or adjusted under 35 U.S.C. 154(b) by 418 days.

(21) Appl. No.: 15/899,382

(22) Filed: Feb. 20, 2018

(65) Prior Publication Data

US 2018/0235178 A1    Aug. 23, 2018

(51) Int. Cl.
| | | |
|---|---|---|
| *G01N 33/22* | (2006.01) | |
| *A01K 15/02* | (2006.01) | |
| *G06K 9/00* | (2006.01) | |
| *G01N 33/00* | (2006.01) | |
| *G01V 8/20* | (2006.01) | |

(52) U.S. Cl.
CPC ......... *A01K 15/02* (2013.01); *G01N 33/0001* (2013.01); *G01N 33/227* (2013.01); *G01V 8/20* (2013.01); *G06K 9/00711* (2013.01)

(58) Field of Classification Search
CPC combination set(s) only.
See application file for complete search history.

(56) References Cited

U.S. PATENT DOCUMENTS

| 4,022,054 A * | 5/1977 | Biederman | ............ A01K 1/035 73/23.34 |
|---|---|---|---|
| 2012/0103060 A1* | 5/2012 | Brasfield | .................. G07C 9/10 73/23.34 |
| 2015/0128866 A1* | 5/2015 | Madorin | ................ A01K 15/02 119/51.01 |
| 2015/0264892 A1* | 9/2015 | Nir | ......................... A01K 15/02 119/795 |
| 2015/0334990 A1* | 11/2015 | Nir | ....................... A61B 5/0077 600/301 |

* cited by examiner

*Primary Examiner* — Xin Y Zhong
(74) *Attorney, Agent, or Firm* — JMB Davis Ben-David

(57) ABSTRACT

Animal-based olfactory detection of one or more target substances in a sequence of filters includes providing one or more enclosures each housing an animal, each enclosure including a sample presenting structure via which only a single olfactory sample is presented to the animal at any given time, presenting samples of the sequence of filters to the animal via the structure, one at a time, and generating an output indication of olfactory detection of target substances in the sequence of filters.

20 Claims, 4 Drawing Sheets

SYSTEM, METHOD AND COMPUTER PROGRAM PRODUCT FOR ANIMAL-BASED OLFACTORY DETECTION

CROSS REFERENCE TO RELATED APPLICATIONS

Benefit is claimed to Israel Patent Application No. 250683, filed Feb. 20, 2017, the contents of which are incorporated by reference herein in their entirety.

FIELD OF THIS DISCLOSURE

The present invention relates generally to olfactory detection and more particularly to animal-based olfactory detection.

BACKGROUND FOR THIS DISCLOSURE

Rodent learning ability has been known for many years.

Animals including dogs and rats are conventionally used to detect odors of interest, e.g. as described in U.S. Pat. No. 7,921,810 to Lumbroso et al. Two approaches are used; the first has the animal search an area for a specific scent ("free-running" approach) whereas the second—the REST (remote explosive scent tracing) approach—collects odors e.g. by suction onto filters, and then, a group of plural filters is simultaneously presented to the dog who sniffs each of the plural filters to determine if the target odor is present or not. If the target odor is present the dog makes a response which the human handler interprets as indicative of presence of a target odor. REST allows a dog to be tested in a climate controlled location, even when the samples are collected in extreme climates. Also, suctioning the odor out of, say, a pallet, vehicle e.g. truck or container, e.g. via a filter, permits the dog to determine if explosives (say) are present, e.g. by sniffing the filter, without having to unload and separate the containers to allow a free-running dog to search. Thus, the REST approach provides considerable savings.

U.S. Pat. No. 4,022,054 to Biederman describes a method and apparatus for use in detecting faint olfactory filters.

Use of a single-hole enclosure for early training of an animal, i.e. presenting just one filter to the animal at a time during a learning phase, is described e.g. in Bodyak, N. and B. Slotnick (1999). "Performance of mice in an automated olfactometer: odor detection, discrimination and odor memory." Chemical Senses 24(6): 637-645.

Once an animal is trained, olfactory detection of unknown samples is conventionally performed using enclosures with plural holders via which plural unknown filter samples are presented simultaneously.

The disclosures of all publications and patent documents mentioned in the specification, and of the publications and patent documents cited therein directly or indirectly, are hereby incorporated by reference. Materiality of such publications and patent documents to patentability is not conceded.

Definition

"Filter" is used throughout the specification and claims to mean a device or material for trapping vapor and dust particles. An example of this is seen in Israel Patent No. 206275.

SUMMARY OF CERTAIN EMBODIMENTS

Certain embodiments of the present invention seek to provide an improved system, and/or method and/or computer program product for animal-based olfactory detection.

Certain embodiments of the present invention seek to provide processing circuitry comprising at least one processor in communication with at least one memory, with instructions stored in such memory executed by the processor to provide functionalities which are described herein in detail.

In accordance with an embodiment of the invention, there is provided a method for animal-based olfactory detection of one or more target substances in a sequence of filters the method including:

providing one or more enclosures each housing an animal, each enclosure including a sample presenting structure via which only a single olfactory sample is presented to the animal at any given time; and presenting samples of the sequence of filters to the animal via the structure, one at a time, thereby to facilitate olfactory detection of target substances in the sequence of samples.

Additionally, the sample presenting structure has an aperture and wherein the method also includes providing a structural element configured to create a predetermined extent of proximity between plural olfactory samples mounted on the structural element and the aperture, one sample at a time.

Furthermore, the structural element has a conveyor external to the one or more enclosures and the method includes moving move one sample at a time into a predetermined extent of proximity with the aperture.

Additionally, each sample includes a filter via which air from an enclosure possibly containing the target odor has been forced.

Furthermore, the one or more enclosures includes at least first and second enclosures and also includes a structural element configured to initially provide a predetermined extent of proximity between plural olfactory samples mounted on the structural element and the aperture in the first enclosure, and to subsequently provide the predetermined extent of proximity between plural olfactory samples mounted on the structural element and the aperture in the second enclosure, wherein proximity is created between samples and each aperture, one sample at a time.

Additionally, a target substance is deemed to have been detected in a sample only if at least a majority of the animals in the at least first and second enclosures detect the substance in the sample.

Furthermore, the method of detection also includes sensing an event in which within a predetermined window of time after presentation of a sample, the animal, having been trained to do so responds to the detection of a target substance by inserting its head into the positive reinforcement dispenser within a predetermined window of time.

Additionally, the step of sensing an event includes sensing an event automatically, by one of the following list:

sensing by use of a proximity detector configured and arranged to sense proximity between the animal and the positive reinforcement dispenser;

sensing by use of a photocell configured and arranged to be activated by the animal itself upon insertion of its head into the positive reinforcement dispenser; and video-monitoring of either or both of the positive reinforcement dispenser and of the animal, thereafter detecting that the animal has approached the dispenser by image processing.

Furthermore, the method also includes employing at least a first positive reinforcement schedule according to which the animal is rewarded, at least during training, for correctly detecting presence of one or more target substances from a sequence of samples.

Additionally, the method may employ at least a second positive reinforcement schedule according to which the animal is rewarded, at least during training, for correctly detecting absence of one or more target substances in the sample.

Furthermore, the method includes depriving the animal of food prior to being placed in an enclosure and rewarding the animal with food for correctly detecting absence of one or more target substances in the samples.

Additionally, olfactory detection of target substances includes the olfactory detection of explosives.

Furthermore, the type of filter, for example, positive control, negative control, unknown or probe, is determined automatically and, responsively, a software program is then instructed regarding a suitable contingency appropriate to that type of filter.

Additionally, each filter bears a visual indication, the method including the step of detecting each the visual indication by photo-sensors.

Furthermore, each filter bears a machine-readable code, the method including detecting the machine-readable code and deriving the filter type, and wherein automatic determination of filter type includes using a video camera positioned to capture the machine-readable code and using one or more pre-stored tables to translate the machine-readable code into filter type.

Additionally, the method also includes sensing when the animal performs an action which the animal has been trained to perform conditional upon target substance presence and providing an olfactory detection output indication accordingly.

In accordance with a further embodiment of the invention, there is provided a system for animal-based olfactory detection of one or more target substances in a sequence of filters, the system including:

a sample presenting structure via which only a single olfactory sample is presented to the animal at any given time; and a processor for presenting samples of the sequence of filters to the animal via the structure, one at a time, and for generating an output indication of olfactory detection of target substances in the sequence of filters.

Furthermore, the sample presenting structure has an aperture and wherein the system also includes a structural element configured to create a predetermined extent of proximity between each of plural olfactory samples mounted on the structural element and the aperture.

Additionally, the structural element has a conveyor external to each enclosure, for moving move one sample at a time into a predetermined extent of proximity with the aperture.

Furthermore, each sample includes a filter via which air possibly containing the target odor has been forced.

Additionally, the one or more enclosures include at least first and second enclosures and also including a structural element configured to initially provide a predetermined extent of proximity between plural olfactory samples mounted on the structural element and the aperture in the first enclosure, and to subsequently provide the predetermined extent of proximity between plural olfactory samples mounted on the structural element and the aperture in the second enclosure, wherein proximity is created between samples and each the aperture, one sample at a time.

Furthermore, the system of detection also includes sensors for automatically sensing an event in which within a predetermined window of time after presentation of a sample, the animal, having been trained to do so responsive to its detection of the one or more target substances removes its nose from the aperture and inserts its head into the positive reinforcement dispenser within a predetermined window of time.

Additionally, the sensors are selected from the following list:

proximity detectors configured and arranged to sense proximity between the animal and the positive reinforcement dispenser;

photocells configured and arranged to be activated by the animal itself upon insertion of its head into the positive reinforcement dispenser; and apparatus including a video-monitor image processing apparatus for monitoring either or both one of the positive reinforcement dispenser and the animal and evaluating the image data so as to assess whether the animal has approached the dispenser, respectively.

Furthermore, each the filter bears a visual indication, and the system includes the step of detecting each the visual indication by photo-sensors.

Additionally, each the filter bears a machine-readable code, and the system includes apparatus for video capture of the machine-readable code and translation of the machine-readable code into filter type.

Also provided, excluding signals, is a computer program comprising computer program code means for performing any of the methods shown and described herein when the program is run on at least one computer; and a computer program product, comprising a typically non-transitory computer-usable or -readable medium e.g. non-transitory computer-usable or -readable storage medium, typically tangible, having a computer readable program code embodied therein, the computer readable program code adapted to be executed to implement any or all of the methods shown and described herein. The operations in accordance with the teachings herein may be performed by at least one computer specially constructed for the desired purposes or general purpose computer specially configured for the desired purpose by at least one computer program stored in a typically non-transitory computer readable storage medium. The term "non-transitory" is used herein to exclude transitory, propagating signals or waves, but to otherwise include any volatile or non-volatile computer memory technology suitable to the application.

Any suitable processor/s, display and input means may be used to process, display e.g. on a computer screen or other computer output device, store, and accept information such as information used by or generated by any of the methods and apparatus shown and described herein; the above processor/s, display and input means including computer programs, in accordance with some or all of the embodiments of the present invention. Any or all functionalities of the invention shown and described herein, such as but not limited to operations within flowcharts, may be performed by any one or more of: at least one conventional personal computer processor, workstation or other programmable device or computer or electronic computing device or processor, either general-purpose or specifically constructed, used for processing; a computer display screen and/or printer and/or speaker for displaying; machine-readable memory such as optical disks, CDROMs, DVDs, BluRays, magnetic-optical discs or other discs; RAMs, ROMs, EPROMs, EEPROMs, magnetic or optical or other cards, for storing, and keyboard or mouse for accepting. Modules shown and described herein may include any one or combination or plurality of: a server, a data processor, a memory/computer storage, a communication interface, a computer program stored in memory/computer storage.

The term "process" as used above is intended to include any type of computation or manipulation or transformation of data represented as physical, e.g. electronic, phenomena which may occur or reside e.g. within registers and/or memories of at least one computer or processor. The term processor includes a single processing unit or a plurality of distributed or remote such units.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively, or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of at least one computer/s or computing system/s, or processor/s or similar electronic computing device/s, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, embedded cores, computing system, communication devices, processors (e.g. digital signal processor (DSP), microcontrollers, field programmable gate array (FPGA), application specific integrated circuit (ASIC), etc.) and other electronic computing devices.

Elements separately listed herein need not be distinct components and alternatively may be the same structure. A statement that an element or feature may exist is intended to include (a) embodiments in which the element or feature exists; (b) embodiments in which the element or feature does not exist; and (c) embodiments in which the element or feature exist selectably e.g. a user may configure or select whether the element or feature does or does not exist.

Any suitable processor/s may be employed to compute or generate information as described herein and/or to perform functionalities described herein and/or to implement any engine, interface or other system described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

Figure 1:
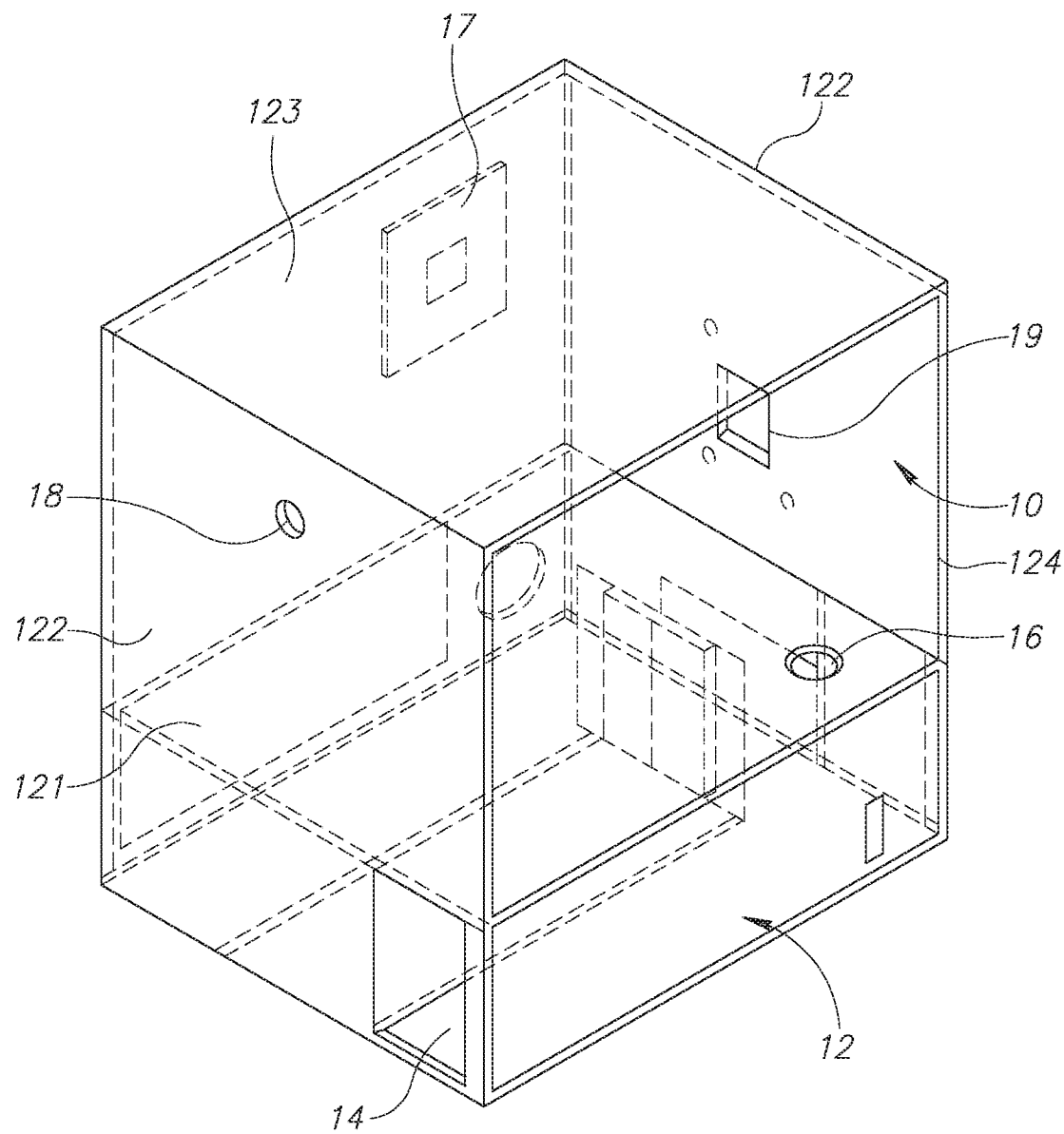
FIGS. 1-3 illustrate an example system for animal-based olfactory detection of one or more target substances in a sequence of filters e.g. filters including enclosures (FIGS. 1, 3), each housing an animal and each including a sample presenting structure e.g. aperture or screen or conduit via which only a single olfactory sample is presented to the animal at any given time; and a conveyor or other structural element (FIGS. 2, 3) configured and operative for presenting samples of the sequence of filters to the animal via the structure, one at a time, thereby to facilitate olfactory detection of target substances in the sequence of filters.

The scale used to illustrate various elements in the drawings is merely exemplary and/or appropriate for clarity of presentation and is not intended to be limiting.

Methods and systems included in the scope of the present invention may include some (e.g. any suitable subset) or all of the functional blocks shown in the specifically illustrated implementations by way of example, in any suitable order e.g. as shown.

Each functionality or method herein may be implemented in software, firmware, hardware or any combination thereof.

Any hardware component mentioned herein may in fact include either one or more hardware devices e.g. chips, which may be co-located or remote from one another.

Any method described herein is intended to include within the scope of the embodiments of the present invention also any software or computer program performing some or all of the method's operations, including a mobile application, platform or operating system e.g. as stored in a medium, as well as combining the computer program with a hardware device to perform some or all of the operations of the method.

DETAILED DESCRIPTION OF CERTAIN EMBODIMENTS

Figure 2:
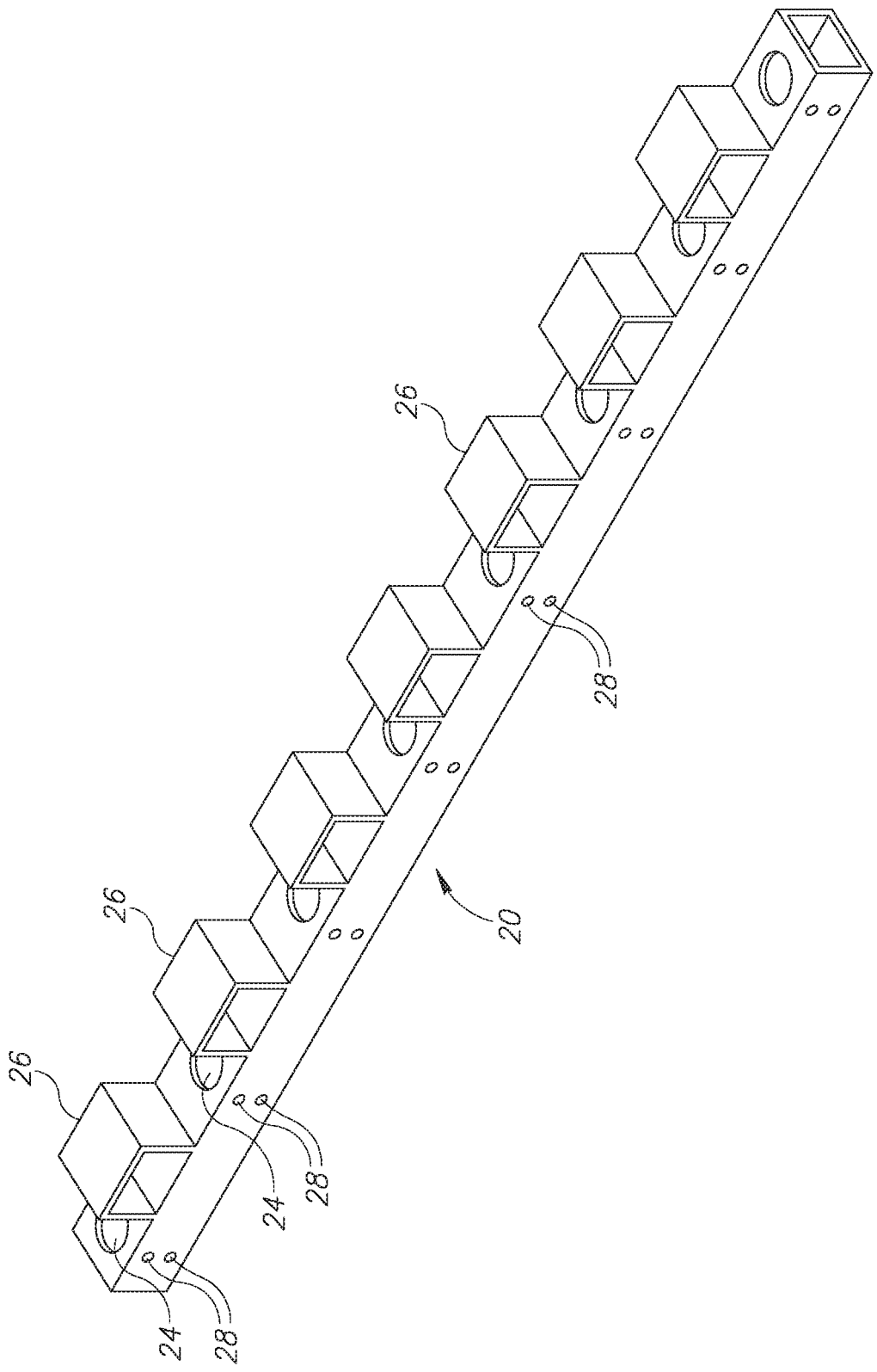
Figure 3:
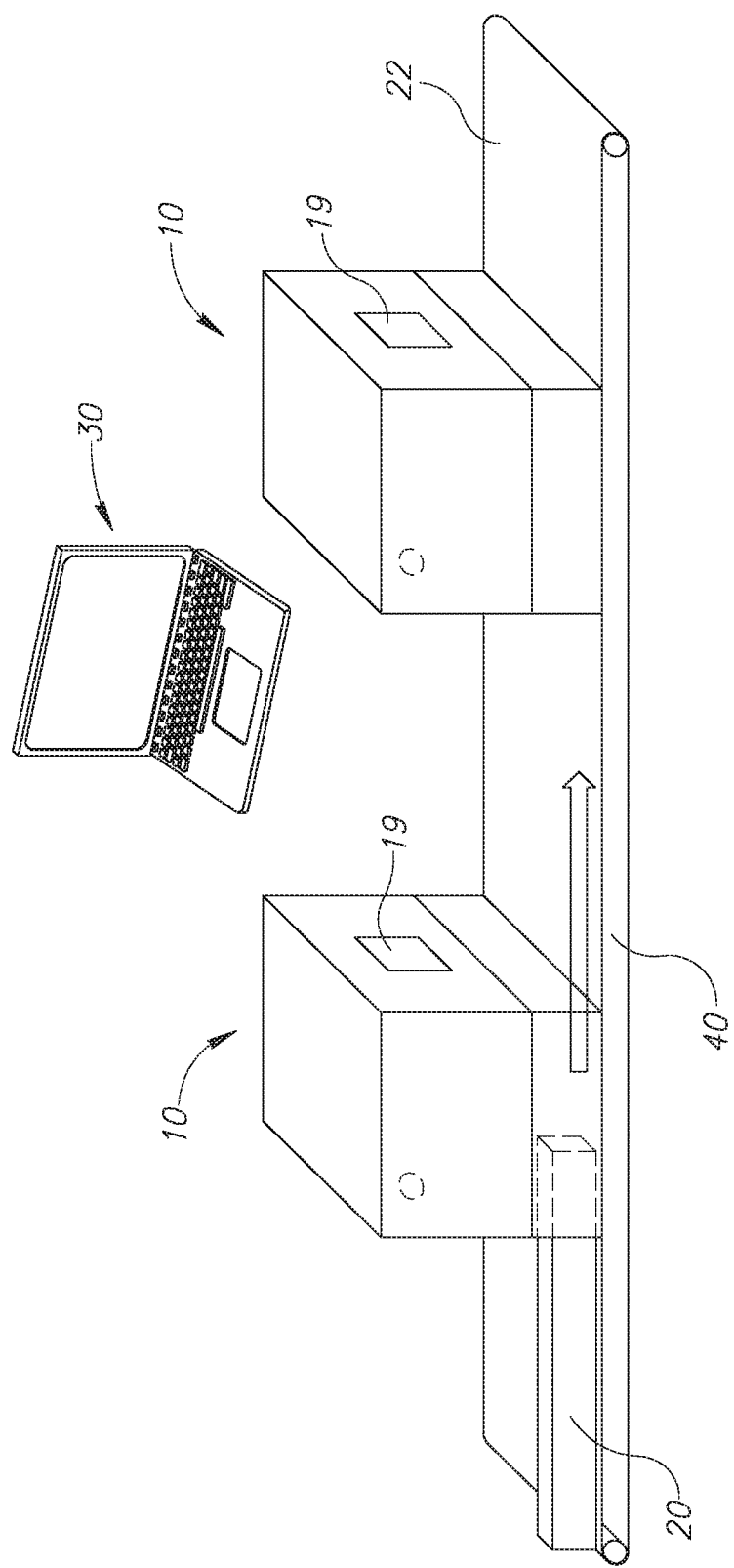

FIGS. 1-3 illustrate an example system for REST odor detection using an animal such as a rodent or rat. For example, a laboratory rat of an outbred strain e.g. a (Sprague-Dawley rat) may be employed. If water or food are used as a reward, the animal may be water or food deprived for several hours. Using a small amount of water or food as a reinforcer allows rats to efficiently make positive detections of many known samples e.g. filters. Play can also be used for reinforcement e.g. for canines, but is more time consuming. Any other suitable reward may be employed such as food or a pleasing auditory or visual or tactile experience.

A test chamber or enclosure 10 (FIG. 1) is used to house the rat who can inspect each filter or other olfactory sample, typically one by one, and report if a target odor is present, having been trained to do so. If the odor is present and the rat reports that it is present, the rat will receive a reward e.g. a small amount of water.

Air sampling to generate odor-bearing filters may proceed in accordance with any of the teachings of any of the following Israel patent documents:

IL 192155—A Method and Apparatus for Detecting Substance to Be Detected Containing At Least One Component That Is Dispersible in Air in The Form of Solid Particles; and/or IL 197142—Apparatus and Methods for Detection of Explosives by Use of Vapour Markers; and/or IL 206275—Apparatus and Methods for Collecting and Analyzing Olfactory Samples.

More generally, olfactory filters e.g. trucks or cargo or containers which are suspected of containing explosives and/or must be searched pursuant to government regulations may be sampled in any desired manner—such as but not limited to filters through which adjacent air containing explosive molecules, has been forced or dust which has been vacuumed from the trucks or cargo or containers.

Photoreceptors may be provided at a suitable location e.g. underneath the floor of the cage or enclosure housing the animal. Alternatively, a camera or bar code reader or QR code reader may be provided in conjunction with suitable visual indication/s on the sample/s e.g. filter/s so as to classify each filter e.g. as known positive, known negative or unknown, and/or type of substance/explosive and/or ID of truck or pallet or container or other suspect substrate from which the sample was taken.

A sled 20 (FIG. 2) may be used for placement of plural filters which contain odor collected, e.g. by suction, from pallets, vehicles, or containers. The sled is translated by a conveyor 40 (FIG. 3) past a suitable odor presentation point in the enclosure, typically so as to present one sample at a time to the animal. As shown in FIG. 3, a local or remote computer 30 is provided which is typically in direct or networked data communication, wired or wireless, with the enclosure of FIG. 1 and/or the sled 20 and conveyor 40, e.g. as described herein in detail, and records the responses to the filters and provides a reward for positive responses (hits) on known filters (filters known to possess the target odor). Typically, even during testing, known positive samples are provided as well as unknown samples e.g. in accordance with a random schedule with a known ratio of known positives vs. unknown. Typically, a reward is provided only for the known positives and not for the unknowns. The ratio of known positives vs. unknown is selected to be high enough to maintain the animal's learned response. If for example, a positive filter is included each (say) 8 filters, literally or on average, the animal remains motivated to inspect unknown samples even though these are not rewarded.

The test chamber 10 is formed of any suitable structural material such as, say, Perspex, and may be of any suitable size; typically 30×30×20 cm is sufficient. Below the test chamber a lower section or basement 12 may be provided some or all of which may serve as a tunnel 14 for insertion and translation of the sled 20. The basement 12 may be equipped with electronic photosensors (not shown). The front part of the lower chamber may serve as the tunnel for insertion and translation of the sled, below a sample presenting structure e.g. an aperture 16 of suitable diameter e.g. 1.5 cm (in the right front section of the chamber in the illustrated embodiment). The aperture 16 is typically large enough to accommodate the animal's snout but not its entire body. This olfactory sample presentation point e.g. aperture is typically close to the reward presentation point if it is desired that the animal spend as little time as possible scampering back and forth between the two.

The test chamber 10 typically has a door (not shown) for insertion and removal of the rat, a ventilating fan 17, a chamber light e.g. LED 18 and (on the right wall in the illustrated embodiment) an opening 19 for providing reward/reinforcement e.g. using any conventional reinforcement delivery system such as the commercial unit produced by Coulbourn Instruments. A sonalert/piezoelectric tone generator may be provided to generate feedback for incorrect responses.

The floor 121, side 122, and back walls 123 may be opaque e.g. black whereas the front wall 124 may be transparent to enable the animal to be observed.

Referring now to FIG. 2, in the illustrated embodiment, the sled 20 includes N e.g. eight or 16 or 30 compartments referenced 24, for the insertion of N filters. Between the filter compartments is a raised barrier 26 which both inhibits movement of the odor between filters and serves as a stop for the movement of the sled between filters. The sled 20 may translate along a runway (not shown) formed of a material which allows smooth movement of the sled e.g. Perspex.

More generally, the sled 20 or other structure may have any suitable configuration which supports and presents sequentially, plural olfactory samples to the aperture 16 in the enclosure 10, without allowing odor in one sample to contaminate the other.

Typically, three types of filters are used in the REST paradigm: a known positive (known to have an explosive odor), known negative filter (known to lack an explosive odor) and unknown or 'probe', used e.g. for testing and/or operations. The unknown or probe filter is of unknown nature, i.e. it is not known whether or not it contains an explosive odor. The computer 30 of FIG. 3 is typically programmed to receive an input which identifies the type of filter currently being presented and to adjust the consequences of the rat's response according to a suitable pre-programmed schedule e.g. a reinforcement reward for some, most or all known positives to which the animal responds correctly, but not for unknowns or probes or for known negatives.

Any suitable implementation may be employed to provide a filter-type identifying input to the computer, e.g. by suitably differentially marking the various filter types. For example, in the illustrated embodiment, the back wall of the sled has two 1 cm diameter holes 28 formed exactly opposite the filter compartments 24. The filter status or type is then determined by two photosensors (not shown) in the lower chamber 12 focused on the two sled wall holes 28 respectively. Then, each type of filter is differentially marked e.g. positive filters have a black band on the upper part of the filter which can be detected by the upper photosensor. Negative filters have the same band on the lower part of the filter which can be detected by the lower photosensor. Thus, the differential activation of the photosensors allow the computer 30 to identify the filter as positive or negative, whereas if neither photosensors is activated, the filter is unknown (if unknown filters have no black bands). Alternatively, any other visual marking of filter types may be employed, and other types of readers may be employed e.g. the photosensors may be replaced with, say, a QR code reader or Bar Code reader. In this case, the holes 28 (FIG. 2) must be sufficiently large to enable the reader to read the QR code of barcode. In one embodiment, the back wall of sled 20 may be removed entirely.

The computer 30 also records the animal's responses as sensed. For example, if a sample is a known positive filter and the rat responds positively, this is recorded as a "hit" (and the rat always or P % of the time, is given a water reward). If the filter is a known positive and the rat fails to respond, the system registers the response as a "miss". If the filter is a known negative filter and the rat responds accordingly, the system registers the response as a "correct reject." If the rat responds inappropriately to the known negative filter the response is recorded as a "false positive" response. If the rat responds to an unknown filter as if it were positive, the system records the response as a YES. If the rat responds as if the filter is negative, they system records the response as a NO.

Any suitable sensor may be used to sense the animal's actions. For example, as shown in FIG. 1, a photosensor may be positioned to sense that the rat has inserted it nose into the aperture 16 via which the samples are presented. Also, a photosensor may be positioned to detect that the rat has inserted its head into the water delivery device 19. The computer 30 typically stores time-stamped indications of these sensor outputs. Thus, the computer 30 can determine the amount of time which elapses from when the rat smells the sample to when the rat interacts with the reward delivery device.

Example

Operation of the system of FIGS. 1-3 may proceed as follows: A rat is placed in the chamber 10 of FIG. 1. Positive, negative and unknown filters are loaded manually or automatically onto the sled 20 of FIG. 2, into each of the holes 24. The sequence of the filters is determined randomly and is also a function of the number of unknown filters that have to be checked. The sled 20 is moved manually or automatically so that the first filter is under the hole 16 in the floor 121 of chamber 10.

According to certain embodiments, once the filter is positioned, the house light 18 turns on providing a signal to the rat to begin checking the filter. If the animal fails to check the sample e.g. filter within a predetermined window of time of (say) one minute, the shift for that animal is terminated e.g. the animal is removed from the enclosure 10 and replaced by another animal. Any suitable sensor e.g. as described herein, may be used to detect that the animal has begun checking the sample e.g. has placed his head in the aperture. If the rat does begin checking e.g. inserts it nose into the aperture 16 above the filter, the system then waits for the animal to remove its nose and make a response. If the filter is positive the rat has a predetermined time window e.g. less than one second e.g. 0.7 or 0.8 seconds or 1.0 seconds to generate its learned response to presence of target odor/s e.g. to put its head into the reward delivery device aperture 19. A suitable time-window duration may be pre-selected by testing for an optimal duration which yields good detections rates e.g. low rates of type 1 and 2 detection errors. If the rat put its head into the water device aperture 19 (or more generally is detected to have approached the reward delivery device), the photocell is activated and responsively, the computer commands the water delivery system to deliver the water reward. If, after removal of its nose from the aperture below which a known negative filter has been presented the rat does not go to the water, this is recorded as a "correct reject" and the light is turned off. The rat only gets rewarded for correct positive responses. Optionally, if the rat puts its head in the water delivery device aperture 19 before inserting its nose into the filter hole 16 a short beep is sounded.

Likewise, a beep may be sounded when the rat makes a false positive response. In the case of unknown filters there is no reward and no beep contingent on the response. Once the rat has made a response the house light 19 is switched off and the rat waits for the next filter. It is appreciated that all or any subset of the occurrences above may be provided, according to various embodiments of the invention.

In a typical display, any of all of the following graphic display elements may be displayed, typically separately on each of 2 screens relating to the 2 (or plural) animals respectively; it is appreciated that the specific icons stipulated below are merely by way of example:

FILTERS—Total number of filters sampled from the start of the shift.
POS—Total number of positive filters since the start of the shift.
MISS—Number of system errors on a positive filter.
HIT—Number of correct identifications of positive filter.
NEG—Total number of negative filters since the start of the shift.
FALSE—Number of system errors on a negative filter.
CORR REJECT—Number of correct identifications of negative filter.
PROBE—Total number of filters from the field (or "unknown" i.e. unknown whether they possess or lack the target odor/s) since the start of the shift.
NO—Number of filters from the field that the system reported as negative.
YES—Number of filters from the field that the system reported as positive.
SENSITIVITY %—Percentage of successful identification of positive filters.
FALSE ALARM RATE %—Percentage of incorrect reporting on negative filters.
SHIFT MIN—Time elapsed since start of shift.
IN UPPER RIGHT SIDE OF SCREEN—Time and date.
STANDBY—System is on standby.
CAGE LIGHT—Filter has entered for sampling.
Detection outcomes which may include, say:
GREEN CIRCLE WITH THE LETTER V—Indicates a negative filter for which the animal has reported that it is indeed negative.
GREEN CIRCLE WITH THE LETTER X—Indicates a false positive.
RED CIRCLE WITH THE LETTER V—Indicates a positive filter that the animal correctly reported as positive.
RED CIRCLE WITH THE LETTER X—Indicates a miss; positive filter that the animal incorrectly reported as positive.
LARGE GREEN CIRCLE—Indicates a filter from the field that the animal has reported as negative.
LARGE RED CIRCLE—Indicates a filter from the field that the animal has reported as positive.

In the illustrated example display, any of all of the following graphic display elements are presented in a suitable manner, to summarize the results of both (or plural) animals together; it is appreciated that the specific icons stipulated below are merely by way of example:

SMALL GREEN SQUARE WITH THE LETTER V—Indicates that both systems reported the correct filter as being negative.
SMALL GREEN SQUARE WITH THE LETTER X—Indicates that both systems reported the incorrect filter as being negative.

SMALL RED SQUARE WITH THE LETTER V—Indicates that both systems reported the correct filter as being positive.

SMALL RED SQUARE WITH THE LETTER X—Indicates that both systems reported the incorrect filter as being positive.

SMALL ORANGE SQUARE—Indicates inconsistency between the two systems.

LARGE RED BLINKING SQUARE—Indicates a filter from the field, which both systems reported as being positive.

LARGE GREEN SQUARE—Indicates a filter from the field, which both systems reported as being negative.

It is appreciated that the example embodiment of FIGS. 1-3 is designed to accommodate a manual option, inter alia, in which a human operator may advance the sled 20 manually to the next filter thereon responsive to an indicator e.g. when a house light 19 is switched off. The house light 19 is controlled to turn off either after the rat gets reinforced or after 0.7 seconds, if that is the window for the rat to make a positive response. Alternatively, the system may be automated in which case the next filter may be presented right after the animal is detected to have responded or after the time window for the animal response has elapsed. In this case, the sled may be replaced by a conveyor 40 more suited for automatic operation.

The computer of FIG. 3 may more generally include any processor programmed for some or all of the following functionalities, which may also be provided stand-alone as a computer program product:

A. provides reinforcement by commanding the reinforcement dispenser reinforcement as per schedule. For example, a VR80% schedule may be used which reinforces 80% of the time, randomly, upon correct detection of a known positive sample, and no reinforcement for unknown samples and for known negatives, if used.

B. issues command to present new filter (e.g. advance conveyor) e.g. if time window has elapsed or if animal detection event has occurred—the earlier of the two C. combines the 2 or more animals' verdict e.g. such that an output indication that the substance is present is provided if and only if both or the majority of the animals have so determined.

In more detail, a processor e.g. the computer of FIG. 3, or stand-alone computer program product, may be operative for all or any subset of the following functionalities:

1. System control functionalities such as all or any subset of:
   a. After a filter is manually (or via the conveyor 40) positioned under the nose hole or aperture, the house light goes on and the software determines the type of filter and then arranges suitable contingencies e.g. all or any subset of:
      i. If the filter is positive and the rat withdraws its nose from the nose hole and the rat inserts its head into the water aperture within, say, 0.7 seconds the rat gets reinforced on a variable ratio schedule (usually 80 to 90 percent of the time). This is registered by the program as a HIT
      ii. If the filter is positive and the rat withdraws its nose from the nose hole and does not insert its head in the water aperture within, say, 0.7 sec the rat does not get water and the non-response is registered as a MISS
      iii. If the filter is negative and the rat withdraws its nose from the nose hole and the rat inserts its head into the water aperture within, say, 0.7 seconds the rat the response is registered as a FALSE POSITIVE.
      iv. If the filter is negative and the rat withdraws its nose from the nose hole and does not insert its head in the water aperture within, say, 0.7 sec the non-response is registered as a CORRECT REJECT
      v. If the filter ID is "unknown" (from the field) and the rat responds within, say, 0.7 sec it does not get reinforced, but the response is registered as a YES ON AN UNKNOWN FILTER
      vi. If the filter ID is "unknown" and the rat does not respond within, say, 0.7 sec the response is registered as a NO ON AN UNKNOWN FILTER
   b. After the rat makes a response the house light is turned off and the rat waits for the next filter.

According to certain embodiments, the user can determine the length of the session, either by a time limit or by the number of reinforcements and/or if the rat fails to put its nose in the filter hole for 1 minute the session is ended where the time-period may be adjustable by the user and/or the duration of the 0.7 sec time window described herein is adjustable by the user and/or the user is prompted by the software to enter the identity of all the filters in a block of eight filters (a full sled) before starting each sled.

2. Data integration functionalities such as all or any subset of:
   a. The same sled is used with two rats or more generally, the same samples are presented to plural animals. In the present example, 2 rats are considered, although 3 or more rats or other animals may be used. If more than 2 rats are used, the decision is based on the majority. First, the rat in unit 1 responds to each filter and the software determines the identity and response to each of the 8 filters on the sled. Then the sled is passed to unit two where the rat in unit 2 responds to each filter and the software determines the identity and response to each of the 8 filters on the sled.
   b. The software then combines the output of each rat to each filter using a suitable preprogrammed rule e.g. the following rule: If both rats respond with a hit to a filter that filter is declared positive. If either rat responds negatively to a filter that filter is declared negative. In the case where there is a discrepancy in response between the two rats, the filter is sampled.

3. Local Data functionalities such as all or any subset of:
   i. The software calculates, and displays, in real time, the sensitivity and selectivity of each rat and of the integrated response to the filters.
   ii. The software displays in real time all or any subset of: total number of filters checked, elapsed time since the start of the shift, number of hits, misses, false positives, and/or correct rejects.
   iii. All of the session data for each shift is stored in a data file and can be analyzed at any time.

4. Data-to-cloud functionalities such as all or any subset of:
   a. The software transmits the response and the response time to each filter of each rat via the internet to the cloud.
   b. The integrated response to each filter is also transmitted to the cloud.

c. The sensitivity and selectivity of each rat can be displayed in real time to anyone authorized to view the data d. The response time for each event can be displayed e. Any suitable user interface may be provided to facilitate easy access to the relevant data by any authorized person.

Figure 4:
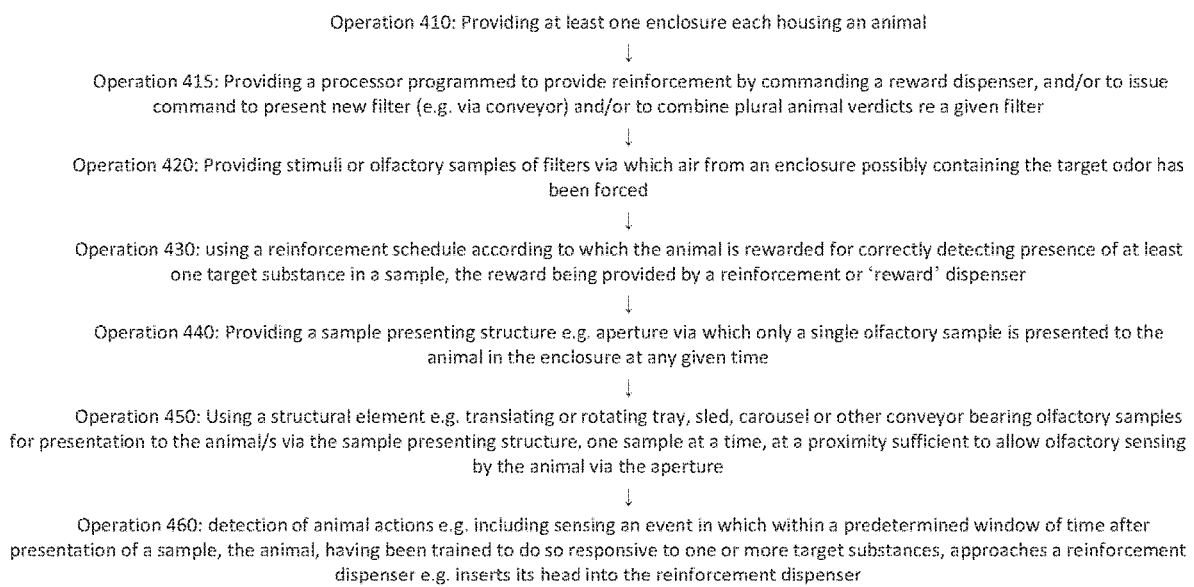
FIG. 4 is a simplified flowchart illustration of an animal-based olfactory detection method in accordance with certain embodiments of the present invention.

FIG. 4 is a simplified flowchart illustration of a method for animal-based olfactory detection of one or more target substances in a sequence of filters. It will be appreciated that included among the various possible results is the possibility that no explosive substance or explosive odor emitting substance is present in the sequence of filters. The method may or may not include all or any subset of the various features of FIGS. 1-3 and may or may not provide some or all of the software functionalities described above. In the method of FIG. 4, some or all of the illustrated operations may be provided, suitably ordered e.g. as follows:

Operation 410: Providing at least one enclosure 10 each housing an animal

Operation 415: Providing a processor programmed to provide reinforcement by commanding a reward dispenser, and/or to issue command to present a new filter (e.g. advance conveyor) and/or to combine plural animal verdicts Operation 420: Providing olfactory samples e.g. filters via which air containing a possible target has been forced.

Operation 430: using a reinforcement schedule according to which the animal is rewarded, at least during training and typically, at least or only for known positive samples, for correctly detecting presence of at least one target substance in a sample, the reward being provided by a reinforcement dispenser also known as 'reward dispenser'.

Operation 440: Providing a sample presenting structure e.g. aperture via which only a single olfactory sample is presented to the animal in the enclosure at any given time Operation 450: Using a structural element e.g. translating or rotating tray, sled, carousel or other conveyor 240 bearing olfactory filters or samples thereof, for presenting the sequence of samples or filters to the animal/s via the sample presenting structure, one sample at a time, at a proximity sufficient to allow olfactory sensing by the animal via the aperture Operation 460: detection of animal actions e.g. including sensing an event in which within a predetermined window of time after presentation of a sample, the animal, having been trained to do so responsive to target substance/s, approaches reinforcement dispenser e.g. inserts its head into the reinforcement dispenser.

It is appreciated that normal operation is preceded by animal training which may proceed in accordance with any suitable animal training method for canines, rodents e.g. rats or other. The animal may be trained to recognize any olfactory substance such as but not limited to one or more explosives e.g. one or more of, say, TNT, RDX, PETN, ammonium nitrate, guns and ammo, fireworks, PX64, SEMTEX, EURODYN2000, doramite, EGDN, nitroglycerin, DNT. Typically, the animal if being trained to recognize odors of several olfactory substances e.g. to respond positively to any of several odors, is first trained on a first olfactory substance, then once training has been completed, the animal is trained on the next and the next. It is found that once a RAT (say) has understood the task, it is very easy to introduce new substances e.g. additional explosives. During training, the animal typically is rewarded using the same reward dispenser later used during testing. The animal may be trained to perform any desired, typically automatically recognizable action upon encountering the target odors and not otherwise. For example, the animal may be trained to approach the reward dispenser e.g. to insert its head past a suitable proximity detector or other sensor deployed in front of the reward dispenser.

Typically, plural animals e.g. rodents e.g. rats sequentially inspect the same samples, as shown in FIG. 3. If plural e.g. two (in the illustrated embodiment) animals are not in accord regarding an unknown filter, it is typically rerun, disregarded, or otherwise processed. Then, the sensitivity (percentage of hits on positive filters) and selectivity (percentage of correct rejects on negative filters) on the combined record of the two rats are both over 90%.

An advantage of certain embodiments is that the rat inspects each filter before the next filter is presented, in contrast to conventional REST systems in which the animal can skip filters.

Another advantage of certain embodiments is automatic sensing of the animal's response in contrast to conventional REST systems, in which there is reliance on human trainer determination of whether the rat made a response or not. This is costly and also allows the trainer to have a significant influence over the response of the animal.

Still another advantage of certain embodiments is simplicity; in prior art devices is in which rodents are expected to interact with 8 or more samples presented via 8 or more respective apertures in the enclosure housing the rodent, it is necessary to provide covers to allow covering each aperture after it has been interacted with to encourage the rodent to interact only with "new" apertures, then uncovering the apertures for another batch of 8 samples once the 8 current samples have finally been smelled by the rodent.

Still another advantage of certain embodiments is that both sensitivity (hits/positives) and selectivity (corrective rejections/negatives i.e. inverse of false alarm rate) for detecting explosives in cargo exceed 90% and even 95%—far in excess of the sensitivity and selectivity characterizing human detection of explosives in cargo.

Yet another advantage of certain embodiments is that olfactory detection includes differentiating between presence and absence of the target substance/s parsimoniously and effectively, by sensing an event in which within a predetermined window of time after presentation of a sample, the animal, having been trained to do so responsive to target substance/s, approaches a reinforcement dispenser e.g. inserts its head into the reinforcement dispenser, rather than, for example, training the animal to remain in contact with positive olfactory samples for at least a predetermined time period and remaining in contact with negative olfactory samples for less than the predetermined time period and then detecting that, or requiring a human attendant to provide a manual input based on that behavior.

The applicability of certain embodiments includes but is not limited to screening of cargo for explosives or narcotics.

It is appreciated that terminology such as "mandatory", "required", "need" and "must" refer to implementation choices made within the context of a particular implementation or application described herewithin for clarity and are not intended to be limiting since in an alternative implantation, the same elements might be defined as not mandatory and not required or might even be eliminated altogether.

The system may if desired be implemented as a web-based system employing software, computers, routers and telecommunications equipment as appropriate.

Features of the present invention, including operations, which are described in the context of separate embodiments may also be provided in combination in a single embodiment. For example, a system embodiment is intended to include a corresponding process embodiment and vice versa. Conversely, features of the invention, including operations, which are described for brevity in the context of a single embodiment or in a certain order may be provided separately or in any suitable subcombination, including with features known in the art (particularly although not limited to those described in the Background section or in publications mentioned therein) or in a different order. Each method may comprise some or all of the operations illustrated or described, suitably ordered e.g. as illustrated or described herein.

We claim:

1. A method performed by at least one processor for animal-based olfactory detection of at least one target substance in a sequence of filters, the method comprising:
   providing at least one enclosure each housing an animal, the enclosure including a sample presenting structure via which only a single olfactory sample is presented to the animal at any given time;
   presenting samples of the sequence of filters one at a time to the animal via the sample presenting structure, thereby facilitating olfactory detection of target substances in the sequence of filters by the animal;
   sensing an event in which, within a predetermined window of time after presentation of a sample, the animal performs a predetermined action signaling detection of said target substance;
   calculating, in real-time, a sensitivity of the animal to each filter of the sequence of filters;
   storing the sensitivity and a time-stamped indication of said animal response; and,
   presenting the sensitivity and the time-stamped indication to a user.

2. A method according to claim 1, wherein the sample presenting structure has an aperture; and,
   wherein the method also comprises providing a structural element configured to create a predetermined extent of proximity between plural olfactory samples mounted on the structural element and the aperture, one sample at a time.

3. A method according to claim 2, wherein the structural element has a conveyor external to the enclosure and the method includes moving one sample at a time into a predetermined extent of proximity with the aperture.

4. A method according to claim 2, wherein each sample includes a filter via which air containing a possible target has been forced.

5. A method according to claim 3, wherein the at least one enclosure comprises at least first and second enclosures and also includes a structural element configured to initially provide a predetermined extent of proximity between plural olfactory samples mounted on the structural element and the aperture in the first enclosure, and to subsequently provide the predetermined extent of proximity between plural olfactory samples mounted on the structural element and the aperture in the second enclosure, wherein proximity is created between samples and each aperture, one sample at a time.

6. A method according to claim 1, wherein said step of sensing an event comprises sensing an event automatically, by one of the list consisting of:
   sensing by use of a proximity detector configured and arranged to sense proximity between the animal and a positive reinforcement dispenser;
   sensing by use of a photocell configured and arranged to be activated by the animal itself upon insertion of its head into the positive reinforcement dispenser; and
   video-monitoring of at least one of the positive reinforcement dispenser and of the animal, thereafter detecting that the animal has approached the dispenser by image processing.

7. A method according to claim 1, further comprising employing at least a first positive reinforcement schedule according to which the animal is rewarded, at least during training, for correctly detecting presence of at least one target substance from a sequence of samples.

8. A method according to claim 7, further comprising depriving animal of food and water prior to being placed in the enclosure, and rewarding the animal with food and water for correctly detecting absence of at least one target substance in the samples.

9. A method according to claim 4 wherein the type of filter is determined automatically and, responsively, a software program is then instructed regarding a suitable contingency appropriate to that type of filter.

10. A method according to claim 9 where each filter bears a visual indication, said method including the step of detecting each said visual indication by photo-sensors.

11. A method according to claim 4, wherein each filter bears a machine-readable code, said method including detecting the machine-readable code and deriving the filter type, and wherein automatic determination of filter type comprises using a video camera positioned to capture the machine-readable code and using at least one pre-stored table to translate the machine-readable code into filter type.

12. A method according to claim 1, further comprising sensing when the animal performs an action which the animal has been trained to perform conditional upon target substance presence and providing an olfactory detection output indication accordingly.

13. A computer program product, comprising a non-transitory tangible computer readable medium having computer readable program code embodied therein, said computer readable program code adapted to be executed to implement a method for animal-based olfactory detection of at least one target substance in a sequence of filters, the method comprising:
   providing at least one enclosure each housing an animal, the enclosure including a sample presenting structure via which only a single olfactory sample is presented to the animal at any given time;
   presenting samples of the sequence of filters one at a time to the animal via the sample presenting structure, thereby facilitating olfactory detection of target substances in the sequence of filters by the animal;
   recording an animal response to presentation of said sequence of filters, said recording obtained by at least one sensor arranged within the structure;
   calculating, in real-time, a sensitivity of the animal to each filter of the sequence of filters;
   storing a time-stamped indication and the sensitivity of said animal response; and,
   presenting the time-stamped indication and the sensitivity to a user.

14. A system for animal-based olfactory detection of target substance/s in a sequence of filters, the system comprising:
   at least one enclosure for housing an animal, each said enclosure including a sample presenting structure via which only a single olfactory sample is presented to an animal at any given time; and
   at least one sensor configured to automatically sense an animal response within a predetermined window of time after presentation of said single olfactory sample, said animal response is an event in which the animal performs a predetermined action signaling detection of a target substance;

a storage configured to store a time-stamped indication of said animal response;

a processor configured to
- presenting samples of the sequence of filters one at a time to the animal via the sample presenting structure, thereby facilitating olfactory detection of target substances in the sequence of filters by the animal;
- recording an animal response, said recording obtained by said at least one sensor arranged within the structure;
- calculating, in real-time, a sensitivity of the animal to each filter of the sequence of filters;
- storing the sensitivity and the time-stamped indication of said animal response in the storage; and,
- presenting the sensitivity and the time-stamped indication to a user, and, a display configured to present said time-stamped indication to a user.

15. A system according to claim 14, wherein said sample presenting structure has an aperture and wherein said system also comprises a structural element configured to create a predetermined extent of proximity between each of plural olfactory samples mounted on the structural element and the aperture.

16. A system according to claim 15, wherein said structural element has a conveyor external to said enclosure, for moving move one sample at a time into a predetermined extent of proximity with said aperture.

17. A system according to claim 16, wherein said at least one enclosure comprises at least first and second enclosures and also comprising a structural element configured to initially provide a predetermined extent of proximity between plural olfactory samples mounted on said structural element and said aperture in the first enclosure, and to subsequently provide the predetermined extent of proximity between plural olfactory samples mounted on said structural element and said aperture in the second enclosure, wherein proximity is created between samples and each said aperture, one sample at a time.

18. A system according to claim 14, wherein said sensors are selected from the list consisting of:
- proximity detectors configured and arranged to sense proximity between the animal and a positive reinforcement dispenser;
- photocells configured and arranged to be activated by the animal itself upon insertion of its head into said positive reinforcement dispenser; and
- apparatus including a video-monitor image processing apparatus for monitoring at least one of said positive reinforcement dispenser and the animal, and evaluating the image data so as to assess whether the animal has approached said dispenser, respectively.

19. A system according to claim 14, wherein each filter of said sequence of filters bears a visual indication, and said system includes the step of detecting each said visual indication by photo-sensors.

20. A system according to claim 19, wherein each said filter bears a machine-readable code, and said system includes apparatus for reading of the machine-readable code and translation of the machine-readable code into filter type.

* * * * *